(12) United States Patent
Higgins et al.

(10) Patent No.: US 10,857,380 B2
(45) Date of Patent: *Dec. 8, 2020

(54) METHOD OF EVALUATING SKIN CONDITIONS

(71) Applicant: Johnson & Johnson Consumer Inc., Skillman, NJ (US)

(72) Inventors: Laura Higgins, Jersey City, NJ (US); Alexandru Paunescu, Clinton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 157 days.

This patent is subject to a terminal disclaimer.

(21) Appl. No.: 16/145,878

(22) Filed: Sep. 28, 2018

(65) Prior Publication Data

US 2019/0099615 A1    Apr. 4, 2019

Related U.S. Application Data

(60) Provisional application No. 62/565,551, filed on Sep. 29, 2017.

(51) Int. Cl.
*A61N 5/06* (2006.01)
*A61B 5/00* (2006.01)
(Continued)

(52) U.S. Cl.
CPC .......... *A61N 5/0616* (2013.01); *A61B 5/0077* (2013.01); *A61B 5/0082* (2013.01);
(Continued)

(58) Field of Classification Search
CPC ................ A61N 5/0616; A61N 5/0621; A61N 2005/073; A61N 2005/0665;
(Continued)

(56) References Cited

U.S. PATENT DOCUMENTS 7,125,416 B2   10/2006   Kent et al.
8,257,416 B2    9/2012   Vanderschuit
(Continued)

FOREIGN PATENT DOCUMENTS

KR   20140136590 A  * 12/2014
KR   20140136590 A    12/2014
(Continued)

OTHER PUBLICATIONS

U.S. Appl. No. 16/145,827, filed Sep. 28, 2018, Johnson & Johnson Consumer Inc.
(Continued)

*Primary Examiner* — Christopher Koharski
*Assistant Examiner* — James Moss

(57) ABSTRACT

A method for at-home skin condition analyses includes coupling an adapter to a port of a wearable lamp platform, placing the wearable lamp platform on a portion of a user's body, coupling a data acquisition device to the adapter and activating the data acquisition device to acquire data pertaining to the user's body through the optical lens, analyzing the data pertaining to the user's body, determining a light treatment regimen for the user's body, and applying light treatment to the user's body according to the determined light treatment regimen. The port has disposed therein an optical lens and having a plurality of image image-acquisition lamps disposed thereabout. The image-acquisition lamps are energized by a power source electrically coupled to the wearable lamp platform, and the wearable lamp platform comprises a plurality of treatment lamps arranged and configured to irradiate a portion of a wearer's body.

15 Claims, 15 Drawing Sheets

(51) Int. Cl.
*A61B 5/103* (2006.01)
*A61N 5/073* (2006.01)

(52) U.S. Cl.
CPC ............ *A61B 5/1032* (2013.01); *A61B 5/441* (2013.01); *A61B 5/442* (2013.01); *A61B 5/4836* (2013.01); *A61B 5/6803* (2013.01); *A61N 5/0621* (2013.01); *A61B 2562/0233* (2013.01); *A61B 2562/04* (2013.01); *A61N 2005/0626* (2013.01); *A61N 2005/0647* (2013.01); *A61N 2005/0652* (2013.01); *A61N 2005/0654* (2013.01); *A61N 2005/0659* (2013.01); *A61N 2005/0661* (2013.01); *A61N 2005/0663* (2013.01); *A61N 2005/0665* (2013.01); *A61N 2005/0666* (2013.01); *A61N 2005/0667* (2013.01); *A61N 2005/073* (2013.01)

(58) Field of Classification Search
CPC .... A61N 2005/0661; A61N 2005/0667; A61N 2005/0666; A61N 2005/0663; A61N 2005/0659; A61N 2005/0654; A61N 2005/0652; A61N 2005/0647; A61N 2005/0626; A61B 5/441; A61B 5/0077; A61B 5/6803; A61B 5/1032; A61B 5/4836; A61B 5/442; A61B 5/0082; A61B 2562/0233; A61B 2562/04
See application file for complete search history.

(56) References Cited

U.S. PATENT DOCUMENTS

| | | | |
|---|---|---|---|
| 8,858,607 B1 | 10/2014 | Jones | |
| 9,370,449 B2 | 6/2016 | Anderson et al. | |
| 2005/0070977 A1* | 3/2005 | Molina | A61N 5/0616 607/88 |
| 2006/0235494 A1 | 10/2006 | Vanderschuit | |
| 2008/0125836 A1* | 5/2008 | Streeter | A61N 5/0618 607/89 |
| 2011/0162673 A1* | 7/2011 | Samain | A45D 44/005 132/317 |
| 2011/0257712 A1* | 10/2011 | Wells | A61B 5/4812 607/90 |
| 2012/0004711 A1 | 1/2012 | Hilty | |
| 2012/0016174 A1 | 1/2012 | De Taboada et al. | |
| 2012/0035689 A1 | 2/2012 | Turtzo | |
| 2013/0066404 A1 | 3/2013 | Tapper et al. | |
| 2013/0274836 A1 | 10/2013 | Downs | |
| 2014/0074010 A1 | 3/2014 | Veres et al. | |
| 2014/0206947 A1 | 7/2014 | Isserow | |
| 2015/0042877 A1* | 2/2015 | O'Neill | G02B 27/0176 348/376 |
| 2015/0065803 A1* | 3/2015 | Douglas | G06T 7/11 600/200 |
| 2015/0127072 A1* | 5/2015 | Pomar | A61N 5/0616 607/90 |
| 2015/0165231 A1 | 6/2015 | Scheja et al. | |
| 2015/0182758 A1* | 7/2015 | Ajiki | A61N 5/0616 607/88 |
| 2015/0290470 A1 | 10/2015 | Tapper et al. | |
| 2016/0038763 A1* | 2/2016 | Tapper | A61N 5/0616 607/88 |
| 2016/0045760 A1* | 2/2016 | Tapper | A61N 5/0616 607/90 |
| 2017/0014264 A1 | 1/2017 | Bradley et al. | |
| 2018/0014777 A1* | 1/2018 | Amir | G06F 19/325 |
| 2018/0106676 A1* | 4/2018 | Jang | G01J 3/2803 |

FOREIGN PATENT DOCUMENTS

KR 101497617 B1 * 3/2015
WO WO2016203461 A1 12/2016

OTHER PUBLICATIONS

International Search Report, Application No. PCT/IB/2018/057571, dated Dec. 19, 2018.

* cited by examiner

METHOD OF EVALUATING SKIN CONDITIONS

CROSS-REFERENCE TO RELATED APPLICATIONS

This application claims the benefit of U.S. provisional application 62/565,551 filed on Sep. 29, 2017,

FIELD OF THE INVENTION

The present invention relates to methods for evaluating skin conditions and delivering light-based skin therapy treatments for improving skin health.

BACKGROUND OF THE INVENTION

Various types of photoanalysis have been developed to enhance the visualization of the skin. They use visible light, polarized light, or ultraviolet light.

Visible light photography, or standard photography, the most common arrangement includes a camera and one or more flash units to deliver visible light to the skin by direct illumination, diffuse illumination, or a combination thereof. Angled visible lighting has also been used to generate a gradient of the illuminating field on the skin to enhance the visualization of wrinkles and fine lines. Depending on the direction of the gradient (vertical or horizontal), different sets of wrinkles and fine lines may be visually enhanced.

Polarized light photography may be used to selectively enhance either surface or subsurface features of the skin. These results are accomplished by placing a polarizing filter (typically a linear polarizing filter) both in front of the flash unit, and in front of the camera. When the polarizing filters are in the same orientation with each other, surface features of the skin such as scales, wrinkles, fine lines, pores, and hairs are visually enhanced. When the polarizing filters are aligned perpendicular to each other, subsurface features of the skin such as erythema, pigmentation, blood vessels, and hair, are visually enhanced.

Ultraviolet photography, where the flash unit is filtered to produce ultraviolet A light and the camera is filtered so that only visible light enters the lens, has also been used to visually enhance the appearance of pigmentation, the bacteria p. acnes, and horns. A variation of ultraviolet photography has been termed the "sun camera" where ultraviolet A light is used to illuminate the skin and an ultraviolet A sensitive film or a digital camera is used to record the reflected ultraviolet light from the skin. In this arrangement, both the pigment distribution and the surface features of the skin are visually enhanced.

In addition to the development of photoanalysis, light therapy for the treatment of skin conditions has also been developed. Light therapy, also known as phototherapy, or heliotherapy, consists of exposure to daylight or to specific wavelengths of light using polychromatic polarized light, lasers, light-emitting diodes, fluorescent light, dichroic light or very bright, full-spectrum light. The light is administered for a prescribed amount of time and, in some cases, at a specific time of day.

Skin disorders treated with light therapy include: atopic dermatitis, psoriasis, vitiligo, acne vulgaris, eczema, neonatal jaundice, and some forms of cancer.

There are many known devices for the administration of light therapy to patients. The size of device needed depends on size of the area that needs treatment. Skin disorders can involve just a few small patches, to nearly the entire body. So, devices for use in skin treatment include floor, countertop or hand-held lamps, as well as wearable patches and masks.

Often, the analysis of the skin condition is made with one device, while the treatment of the skin condition is performed with another device. The present invention provides a kit combining photoanalysis and light therapy.

SUMMARY OF THE INVENTION

Surprisingly, we have found a method that provides a simple and elegant solution to providing economic, at-home skin condition analyses. The method includes coupling an adapter to a port of a wearable lamp platform. placing the wearable lamp platform on a portion of a user's body, coupling a data acquisition device to the adapter and activating the data acquisition device to acquire data pertaining to the user's body through the optical lens, analyzing the data pertaining to the user's body, determining a light treatment regimen for the user's body, and applying light treatment to the user's body according to the determined light treatment regimen. The wearable lamp platform has an outer surface and an inner surface. The port has disposed therein an optical lens and having a plurality of image image-acquisition lamps disposed thereabout. The image-acquisition lamps are energized by a power source electrically coupled to the wearable lamp platform, and the wearable lamp platform comprises a plurality of treatment lamps arranged and configured to irradiate a portion of a wearer's body.

kit comprising a wearable lamp platform a frame for holding the wearable lamp platform in a fixed orientation spaced from the user's body, an adapter arranged and configured to couple a data acquisition device to the optical lens of the at least one port; and a power source controller electrically coupled to the wearable lamp platform provides a simple and elegant solution to providing economic, at-home skin condition analyses. The wearable lamp platform includes a plurality of treatment lamps arranged and configured to irradiate a portion of a wearer's body, and at least one port extending through the lamp platform from the outer surface to the inner surface. The at least one port has disposed therein an optical lens and a plurality of image-acquisition lamps disposed thereabout. The inner surface of the wearable lamp platform is reflective and is arranged and configured to reflect light scattered by the wearer's body back to the body, and the at least one port and the adapter are arranged and configured to couple in a single operative position.

DETAILED DESCRIPTION OF THE INVENTION

Figure 1:
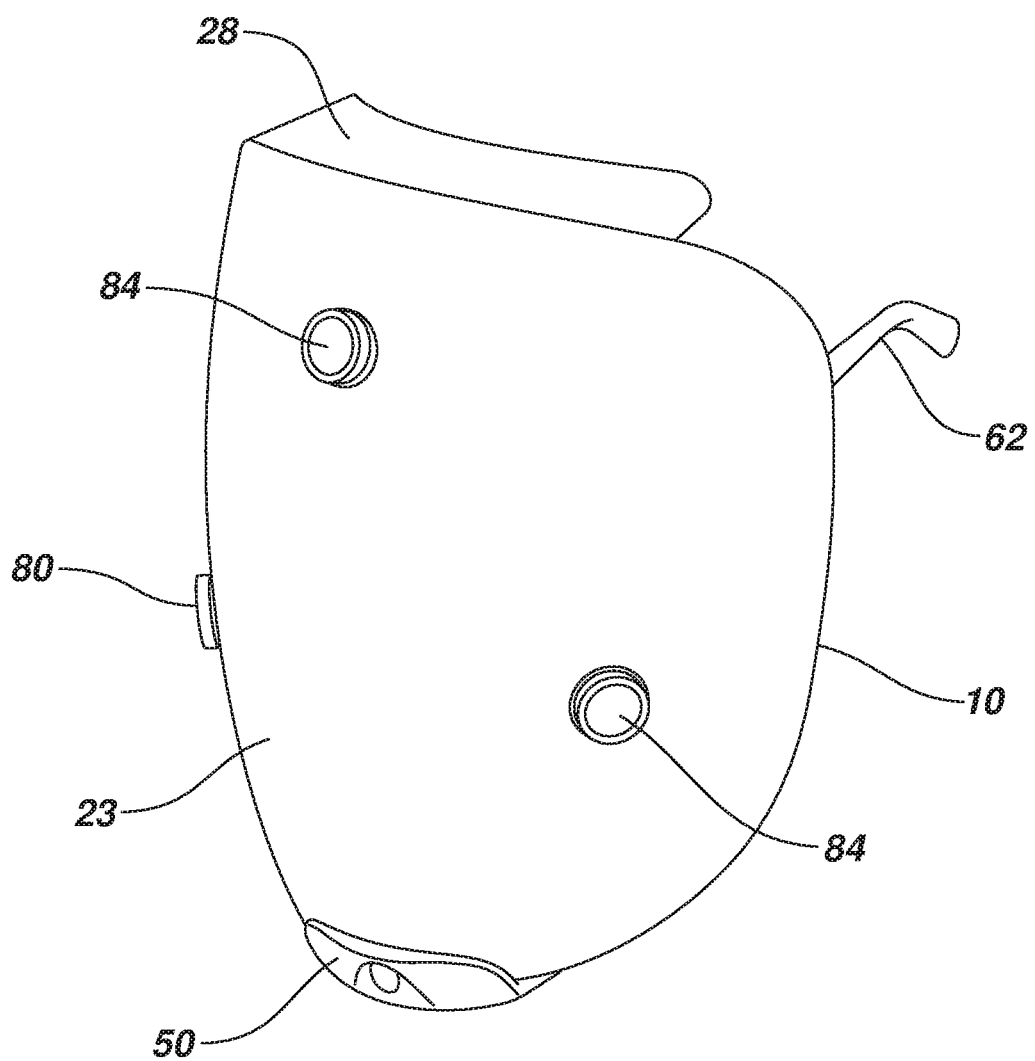
FIG. 1 is a front perspective view of a first embodiment of a diagnostic treatment kit comprising a wearable lamp platform.
Figure 2:
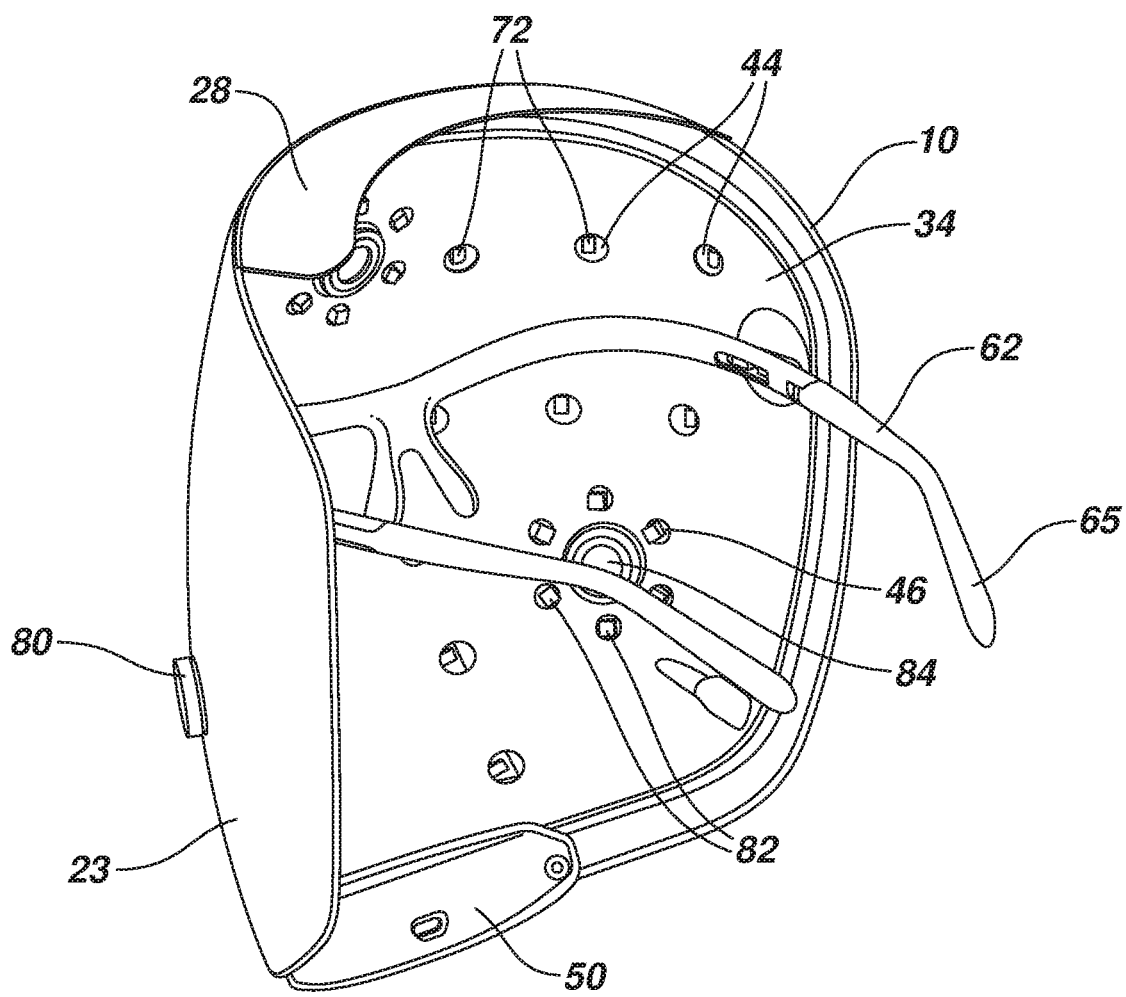
FIG. 2 is a rear perspective view of the kit of FIG. 1.
Figure 3:
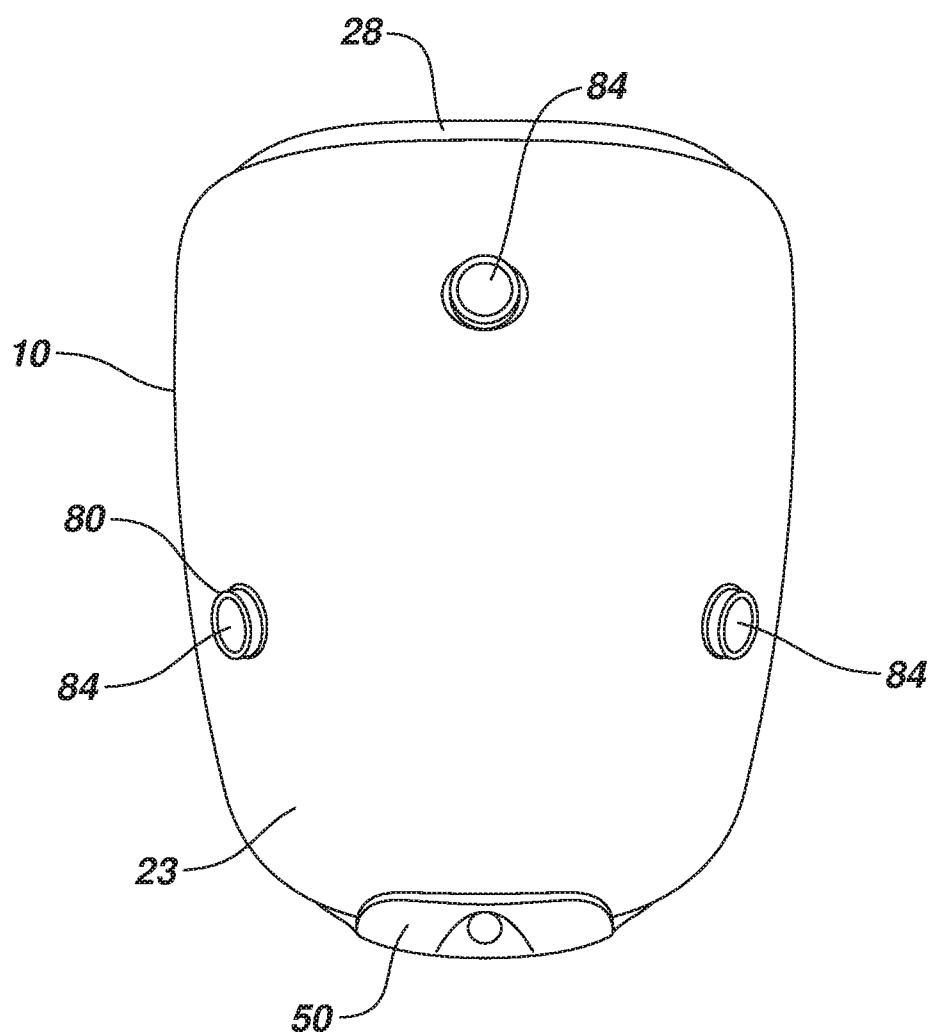
FIG. 3 is a front view of the kit of FIG. 1.
Figure 4:
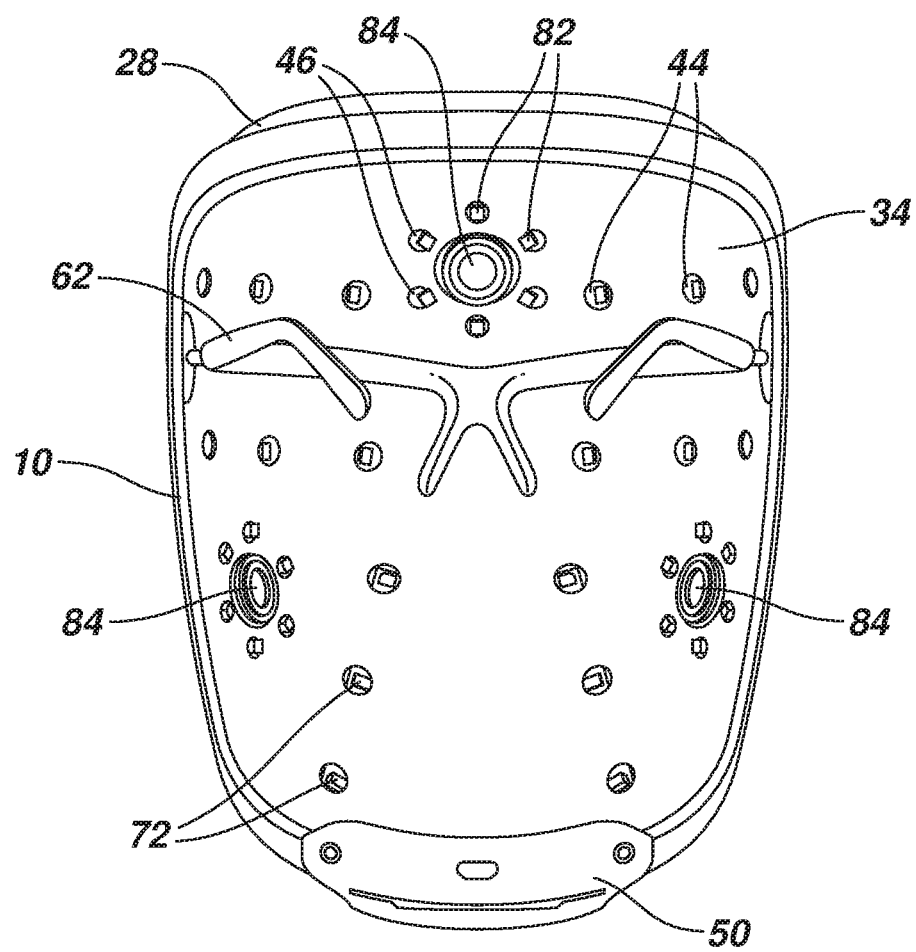
FIG. 4 is a rear view of the kit of FIG. 1.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs.

The present invention relates to kits and methods for evaluating skin conditions, and delivering light-based skin therapy treatments for improving skin health, such as anti-aging enhancement or acne prevention, using light radiating sources. In some embodiments, the kit is wearable and hands-free.

FIGS. 1-9 show a first embodiment of a wearable diagnostic treatment kit in the form of a wearable mask. In this embodiment, the kit includes a wearable lamp platform 10, a frame 60 for holding wearable lamp platform 10 in a fixed orientation spaced from the user's body, an adapter 92 arranged and configured to couple a data acquisition device to wearable lamp platform 10, and a power source controller 50 electrically coupled to the wearable lamp platform 10.

Wearable lamp platform 10 has an outer wall first surface 23 and an inner wall second surface 34, a plurality of treatment lamps 72 arranged and configured to irradiate a portion of a wearer's body, and optical lens ports 26 extending through lamp platform 10 from outer wall first surface 23 to inner wall second surface 34. Disposed in optical lens ports 26 are optical lenses 84.

In this embodiment, wearable lamp platform 10 has a flexible skirt 28 disposed at one end of platform 10. Flexible skirt 28 is arranged and configured to block ambient light from the portion of a wearer's body under treatment. In other embodiments, flexible skirt 28 may be disposed about the periphery of wearable lamp platform 10 and arranged and configured to optically isolate the portion of a wearer's body from ambient light sources. In still other embodiments, wearable lamp platform 10 lacks a flexible skirt 28.

Inner wall second surface 34 of wearable lamp platform 10 is reflective and is arranged and configured to reflect light scattered by the wearer's body back to the body.

Figure 5:
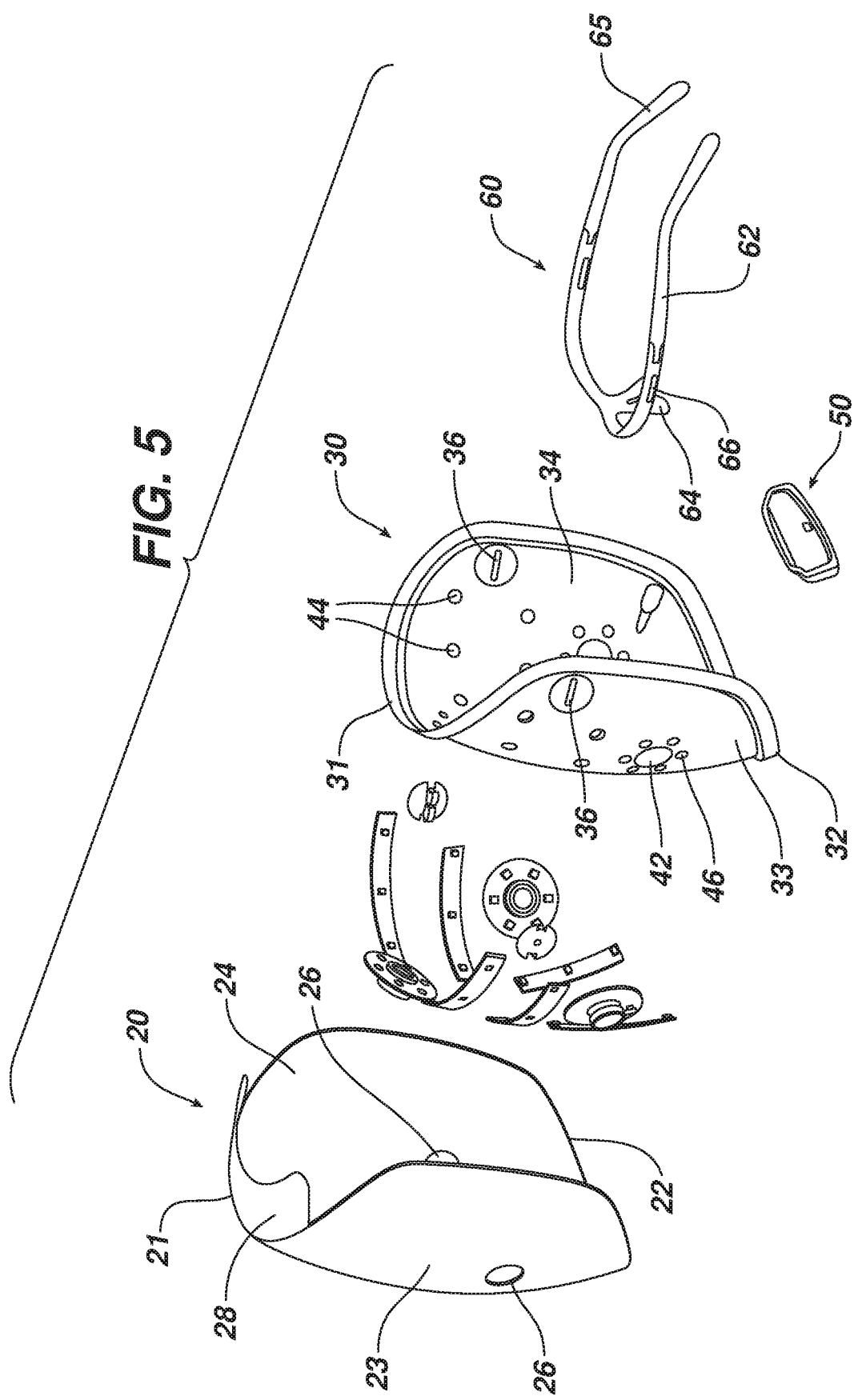
FIG. 5 is an exploded perspective view of FIG. 2.

FIG. 5 is an exploded perspective view of wearable lamp platform 10. As seen in the figure, wearable lamp platform 10 is comprised of an outer wall 20 and an inner wall 30. Outer wall 20 is disposed furthest away from the portion of the wearer's body receiving treatment, while the inner wall 30 is disposed closer thereto. The walls have a concave configuration in both horizontal and vertical directions, where the concavity comprises a multi-dimensional parabolic curvature for catching and reflecting the radiation back to the treatment areas. In this embodiment, where the treatment kit has the structure of a wearable mask, the walls are constructed of a plastic material having a malleable rigidity so that wearable lamp platform 10 can be bent and deflected slightly during use. It is intended that the concavity is slightly smaller than the head of the user so that the mask has to be bent out when applied thereby providing a close but comfortable tightness on the user which will keep the wearable lamp platform 10 in a desired position during use.

Outer wall 20 has a first end 21, a second end 22, an outer wall first surface 23, an outer wall second surface 24, several optical lens ports 26 extending through outer wall 20, and flexible skirt 28 disposed on first end 21 of outer wall 20. As previously mentioned, flexible skirt 28 is arranged and configured to block ambient light from the portion of a wearer's body under treatment, and may be disposed about the periphery of wearable lamp platform 10 and arranged and configured to optically isolate the portion of a wearer's body from ambient light sources. Disposed in optical lens ports 26 are optical lenses 84.

Inner wall 30 has a first end 31, a second end 32, an inner wall first surface 33, an inner wall second surface 34, snap-out pivotal connections 36, optical lens ports 42, treatment lamp apertures 44, and image-acquisition lamp apertures 46. Ports 42, and apertures 44 and 46 all extend through inner wall 30. Inner wall 30 is comprised of a smooth seamless reflective surface facing the treatment area.

Outer wall 20 and inner wall 30 have different radii of concavity. When wearable lamp platform 10 is assembled, the entire perimeter is sealed as outer wall 20 and inner wall 30 come together. Such a mating seal is typically effected through a sonic weld arrangement. Alternatively, local sealing points (not shown) can be employed to assemble the walls together with spaced intermediate seals. As far as the user is concerned wearable lamp platform 10 presents an integral structure.

When wearable lamp platform 10 is assembled, treatment lamp apertures 44 are matingly aligned relative to treatment lamps 72 so that lamps 72 can radiate the therapeutic light through apertures 44. Accordingly, treatment lamps 72 are recessed relative to inner wall 30 to preclude contact with the treatment surface and to make it very difficult for treatment lamps 72 themselves to be in any way contacted by the user. Such an assembly results in a controlled communication of radiating therapy in a manner to impart a predetermined cone of therapeutic light on to a treatment area. The apertures are disposed relative to desired treatment areas and wall parabolic configuration for even light distributions across the treatment area. A combination of such a controlled cone of light, predetermined disposition of treatment lamps 72 themselves on lamp platform 10, an inner reflective surface on the inner wall 30, and a controlled positioning of the assembly relative to the treatment area via a platform position relative to contact areas of the nose and the ears, presents an assembly which presents a highly predictable distributive pattern of the light (predetermined cones of light per light source), thereby minimizing the number of treatment lamps 72 that need to be included for effective treatment.

Also, when wearable lamp platform 10 is assembled, image-acquisition lamps 82 are disposed in image-acquisition lamp apertures 46. Image-acquisition lamps 82 work in concert with optical lenses 84 to acquire data pertaining to the user's body through optical lenses 84.

Figure 6:
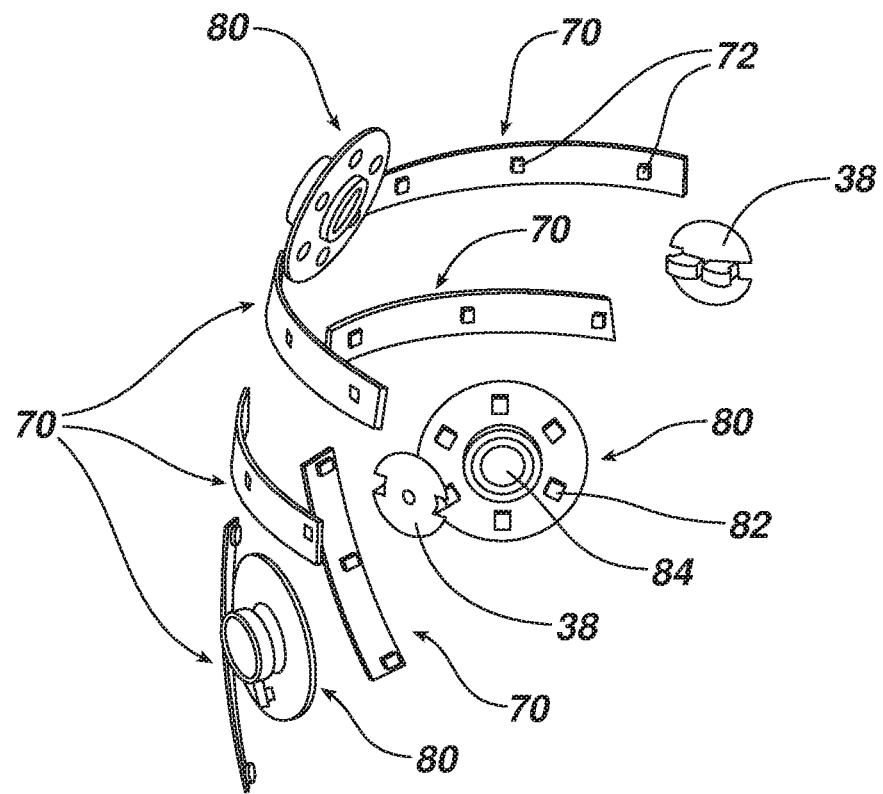
FIG. 6 is a perspective view of a section of FIG. 5.

In addition, when assembled, there is a spacing between outer wall 20 and inner wall 30 of wearable lamp platform 10. Disposed in the spacing, for enhanced safety and convenience purposes, are lamps, lenses and the circuitry connecting the lamps to power source controller 50. As shown in FIG. 6, treatment lamps 72 are disposed on treatment lamp platforms 70, and image-acquisition lamps 82 and optical lenses 84 are disposed on image-acquisition platforms 80. Snap-out pivotal connection bodies 38 are also disposed in the spacing between outer wall 20 and inner wall 30. Though not shown in the drawings, circuitry connects power source controller 50 to treatment lamps 72 and image-acquisition lamps 82. The circuitry may be in the form of conductive wires or filaments. They may be made of metallic or nonmetallic conducting materials. Metallic conducting materials include copper, aluminum and silver. Nonmetallic conducting materials include graphite or conductive polymers.

In some embodiments, outer wall 20 primarily functions as a support for the lamps, lenses and the circuitry. Alternatively, the lamps could be fixed to the inner wall 30. Regardless of which wall supports the lamps, treatment lamps 72 need to be properly aligned with treatment lamp apertures 44, and image-acquisition lamps 82 must be disposed in image-acquisition lamp apertures 46 to achieve desired performance of wearable lamp platform 10.

When wearable lamp platform 10 is assembled, power source controller 50 is disposed on and attached to second end 22 of outer wall 20 and second end 32 of inner wall 30. Power source controller 50 has various components like resistors, ICs (Integrated Circuits), capacitors, transformers, switches, batteries, and other components. The source of power is typically batteries, which in some embodiments may be rechargeable.

Frame 60 is used for holding wearable lamp platform 10 in a fixed orientation spaced from the user's body. Frame 60 has temple arms 62, nose arms 64, and connectors 66. Temple arms 62 are the long arms on the sides of frame 60 that extend over the ears to keep frame 60 on the user's face. In this embodiment, formable ear latches 65 are included as part of the temple arms 62. Nose arms 64 hold wearable lamp platform 10 in a set distance from the user's face. Connectors 66 attach frame 60 to snap-out pivotal connections 36 on inner wall 30. In some embodiments, frame 60 may also have interchangeable lenses can be used to provide eye protection. In some embodiments, temple arms 62 may telescope for better sizing relative to the head size of the user, or could include a head strap to secure wearable lamp platform 10 to the user.

Snap-out pivotal connections 36 allow wearable lamp platform 10 to pivot relative to frame 60 so that a user may adjust light intensity relative to a treatment area by moving the platform closer or farther away. As noted above, platform 10 is flexible with a concave parabolic bias, but still has a malleable rigidity. When frame 60 is received on the user, it is disposed to expand platform 10 parabolic bias to form a match to the size of the user. Frame 60 reference contact points to the user may comprise the temples, the nose bridge and the ears of the user.

Treatment lamps 72 may be Light Emitting Diodes (LEDs), or other radiant energy forms. This includes fluorescents, lasers, infrareds, ultraviolet or combinations of radiant energy forms. Methods of manipulating the light energy are encompassed within the present embodiments. Other methods of light emission may comprise continuous, pulsed, focused, diffuse, multi-wavelength, single wavelength, visible and/or non-visible light wavelengths.

Treatment lamps may provide blue light having a wavelength of between about 450 nm and about 495 nm, or red light having a wavelength of between about 620 nm and about 700 nm, or infrared light having a wavelength of between about 700 nm and about 1 mm.

First embodiment wearable lamp platform 10 has a total of eighteen treatment lamps 72 arranged in an orderly pattern to cover the jaw line, chin, cheek, nose, and forehead, but not the eyelids of the user. The number, arrangement, type, and color of treatment lamps 72 depends on the desired treatment. Desired treatments include, but are not limited to, skin disorders, such as acne vulgaris, atopic dermatitis, psoriasis, vitiligo, scleroderma, eczema, fine lines and wrinkles, as well as neonatal jaundice and some forms of cancer. For example, if the desired treatment is for skin acne blue and red LEDs would be used, as these frequencies are most useful for acne treatment. A minimum number of treatment lamps 72 are intended, with there still being enough to provide effective treatment.

Image-acquisition lamps 82 work in concert with optical lenses 84 to acquire data pertaining to the user's body through optical lenses 84. Image-acquisition lamps 82 could be LEDs or other radiant energy forms. In first embodiment wearable lamp platform 10, three sets of image-acquisition lamps 82 and optical lenses 84 are shown. In this embodiment, the optical lenses 84 are arranged to cover the chin, cheek, nose, and forehead. However, in other embodiments, the number of sets of image-acquisition lamps 82 and optical lenses 84, as well as the arrangements of these sets, are possible, depending on the desired images. In addition, in some embodiments, one or more of optical lens 84 may be a wide-angle lens.

First embodiment wearable lamp platform 10 has a total of eighteen image-acquisition lamps 82 arranged in a circular pattern around each optical lens 84. However, the number, arrangement, type, and color of image-acquisition lamps depends on the desired images.

Figure 7:
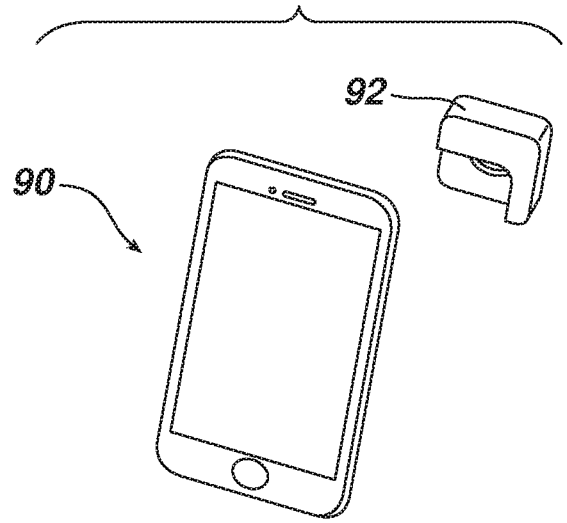
FIG. 7 is a front perspective view of one embodiment of a data acquisition device that can be used in conjunction with the wearable lamp platform of FIG. 1.

As mentioned earlier, the wearable diagnostic treatment kit includes an adapter arranged and configured to couple a data acquisition device to the wearable lamp platform. FIG. 7 is a front perspective view of one embodiment of a data acquisition device 90 that can be coupled to wearable lamp platform 10 by adapter 92. Adapter 92 couples to any of the optical lenses 84 disposed in any of optical ports 26. In some embodiments, data acquisition device 90 is a camera. In these embodiments, adapter 92 is selected to couple the camera lens of the camera to any of the optical lenses 84 disposed in any of optical lens ports 26. In other embodiments, such as that shown in FIGS. 7 to 9, data acquisition device 90 is a smart phone. In these embodiments, adapter 92 is selected to couple the camera lens the smart phone to any of the optical lenses 84 disposed in any of optical lens ports 26.

In some embodiments, data acquisition device 90 has at least one data processing component. The data processing component can use visible light to analyzes skin color, polarized light to analyze surface or subsurface features of the skin, or ultraviolet light enhance the appearance of pigmentation, the bacteria p. acnes, and horns.

Figure 8:
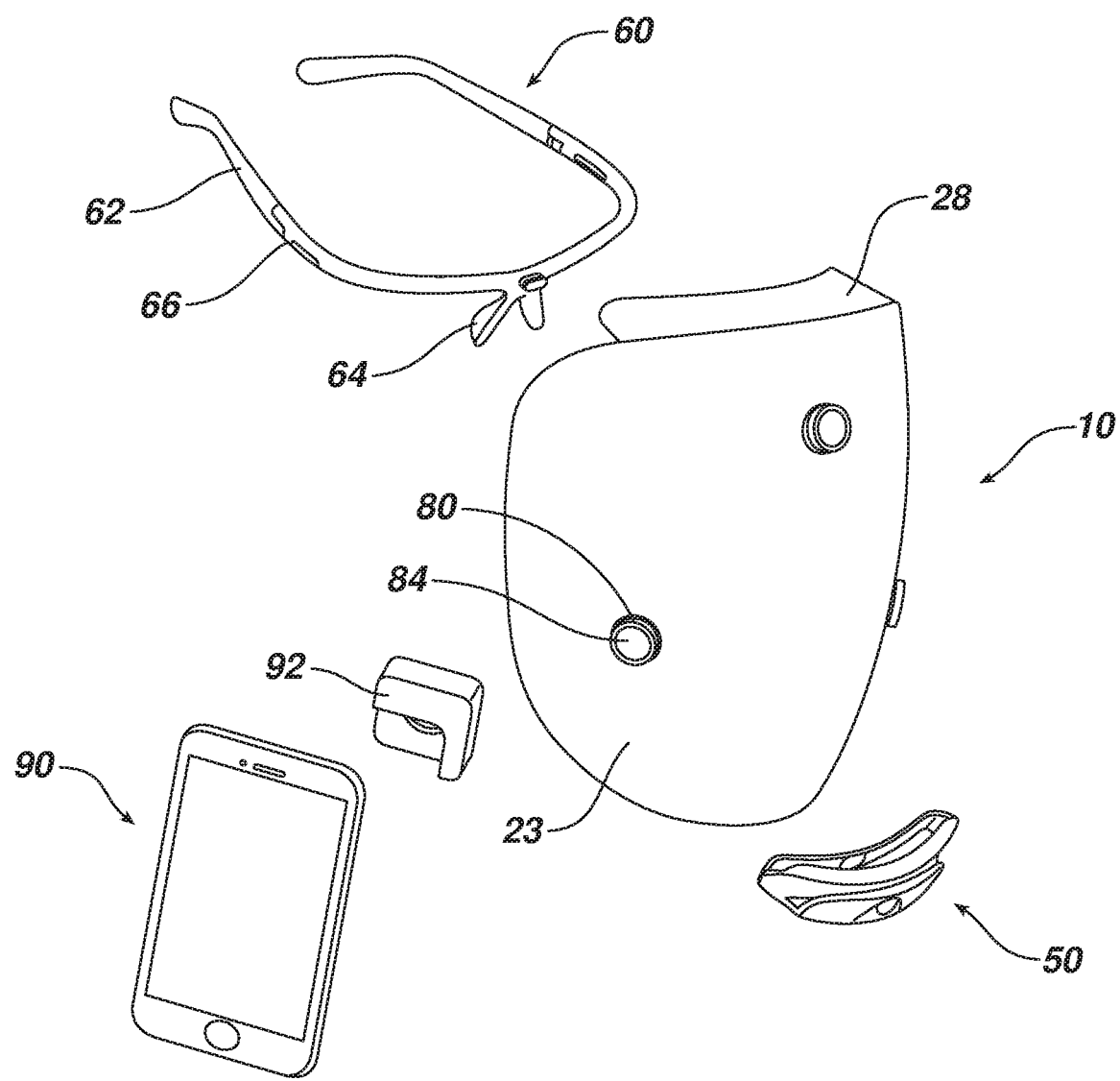
FIG. 8 is a partially exploded perspective view of the kit of FIG. 1 with the data acquisition device of FIG. 7 not coupled to the wearable lamp platform.

FIG. 8 is a partially exploded perspective view of the first embodiment kit of the present invention. The kit includes wearable lamp platform 10, frame 60, power source controller 50, and adapter 92. Data acquisition device 90 is not coupled to wearable lamp platform 10.

Figure 9:
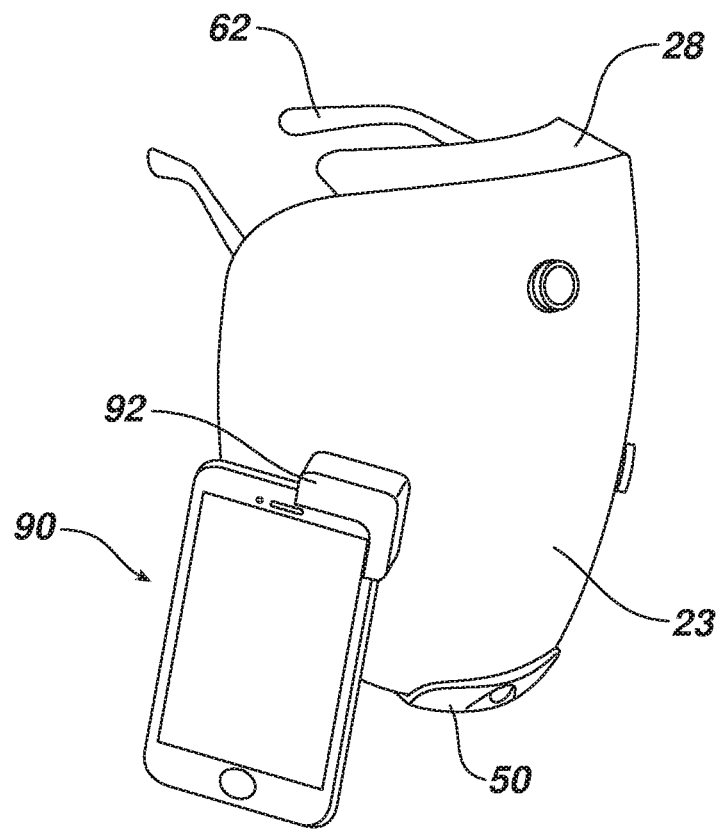
FIG. 9 is a front perspective view of the kit of FIG. 1 with a data acquisition device of FIG. 7 coupled to an optical lens of at least one port of the wearable lamp platform.
Figure 10:
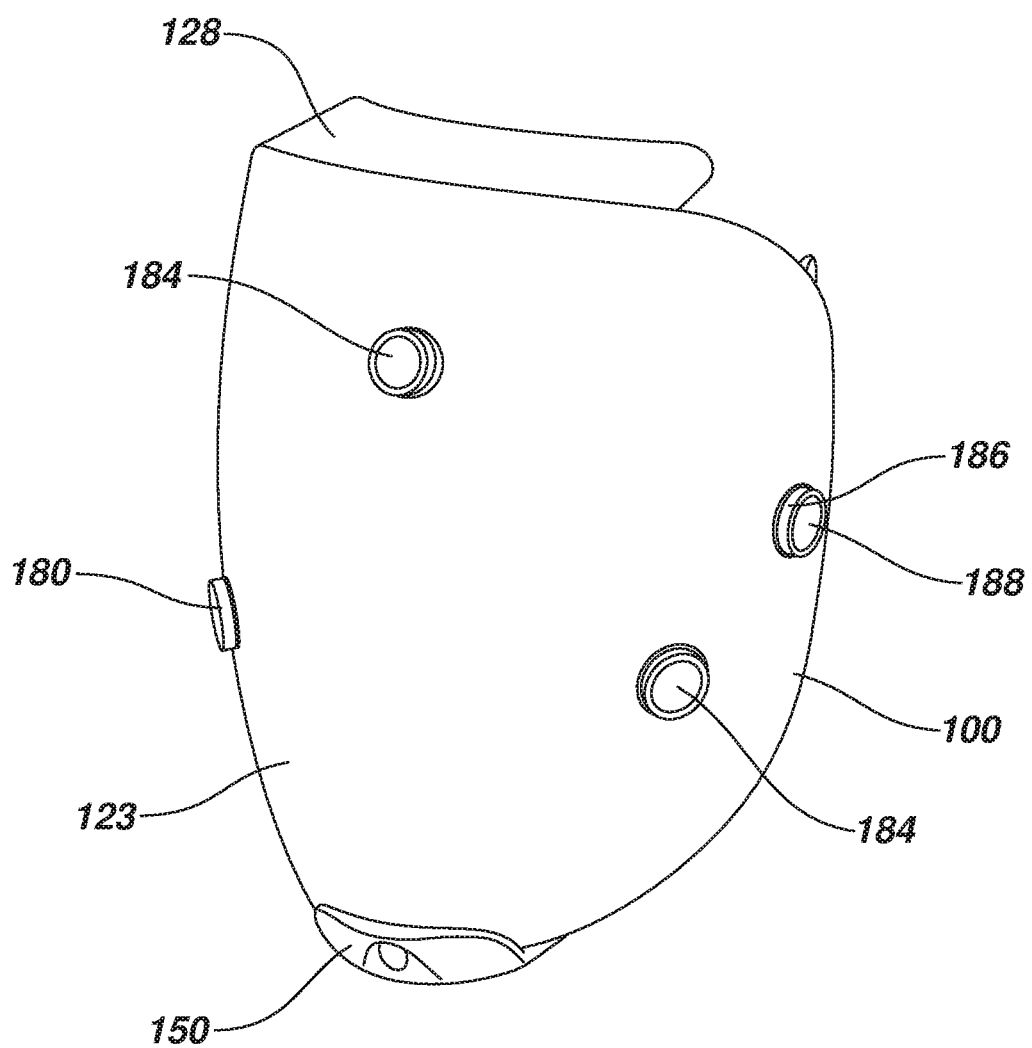
FIG. 10 is a front perspective view of a second embodiment of a diagnostic treatment kit comprising a wearable lamp platform.
Figure 11:
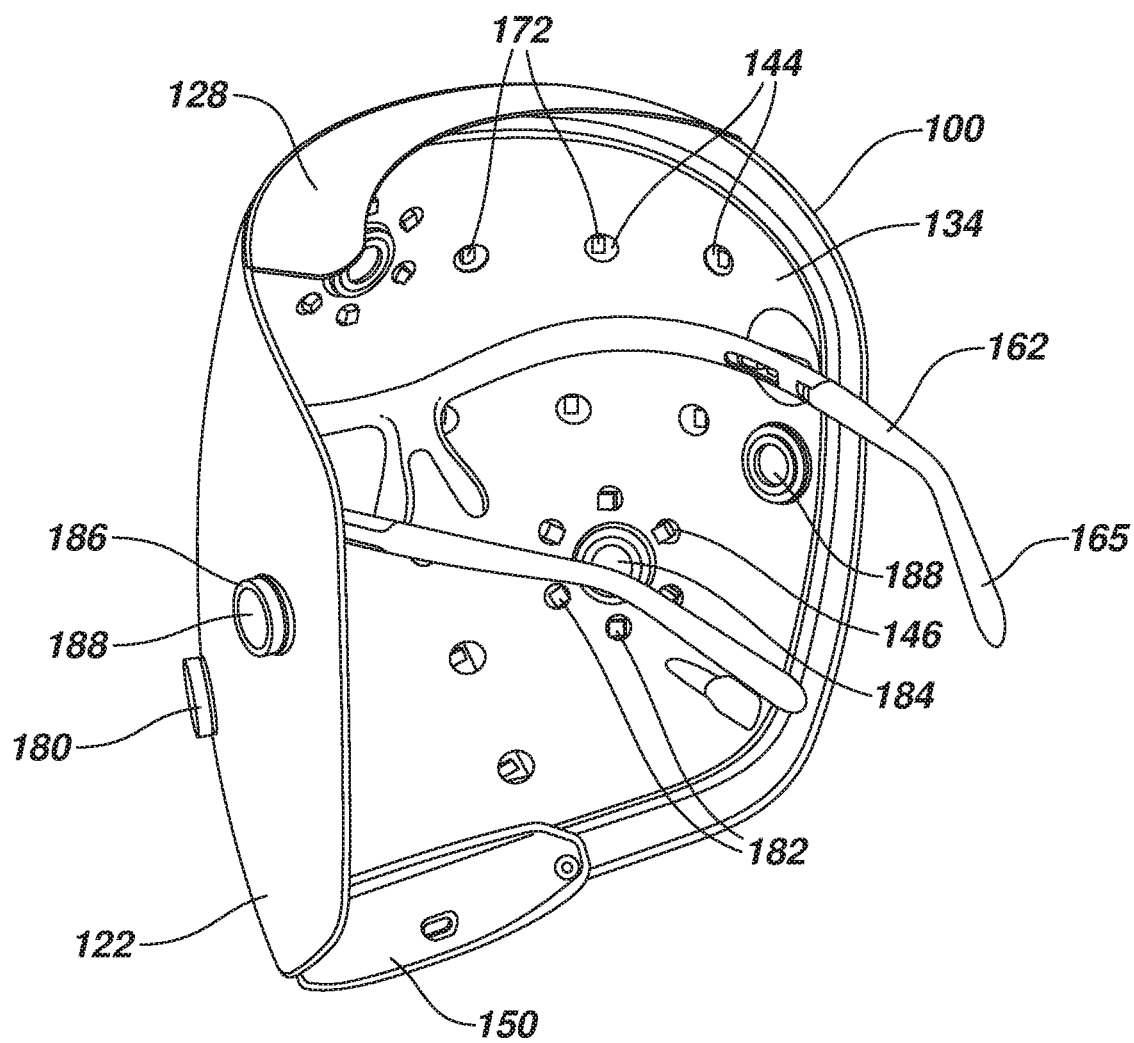
FIG. 11 is a rear perspective view of the device of FIG. 10.
Figure 12:
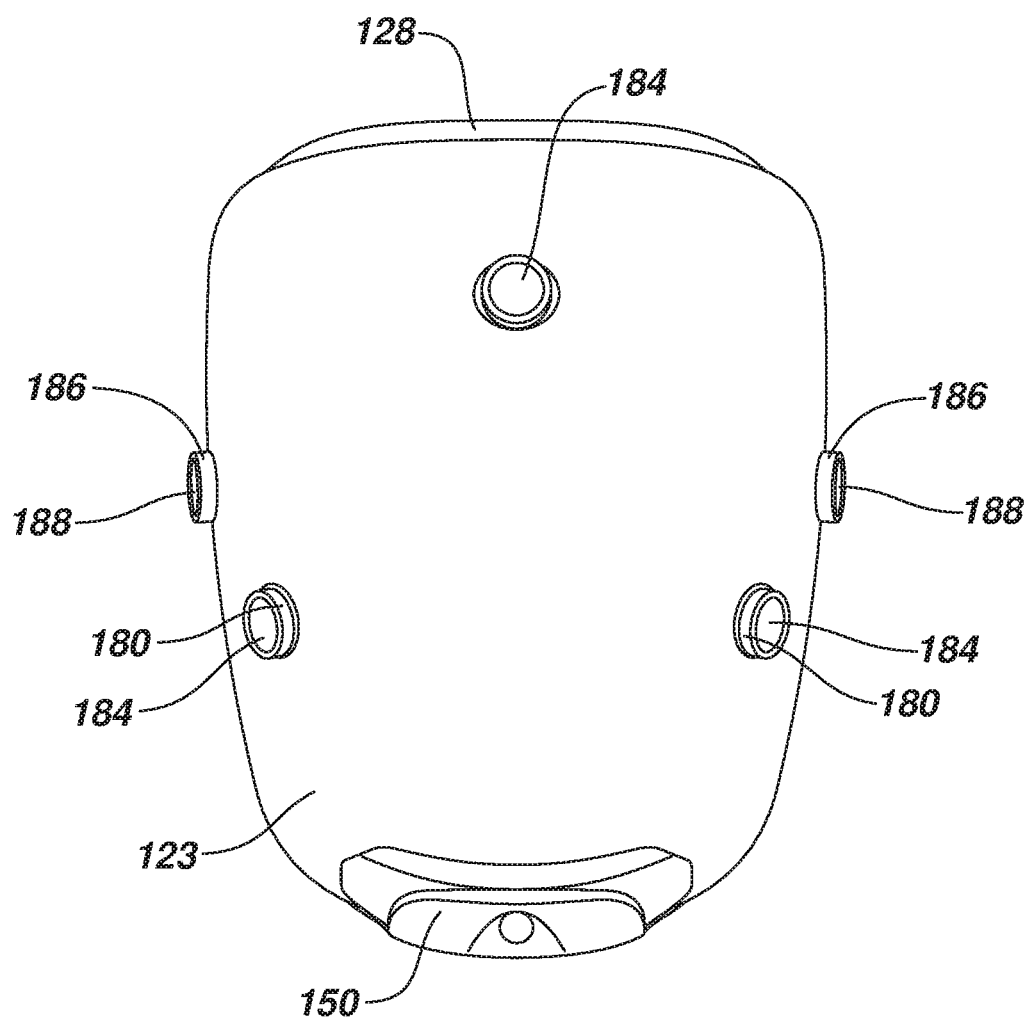
FIG. 12 is a front view of the device of FIG. 10.
Figure 13:
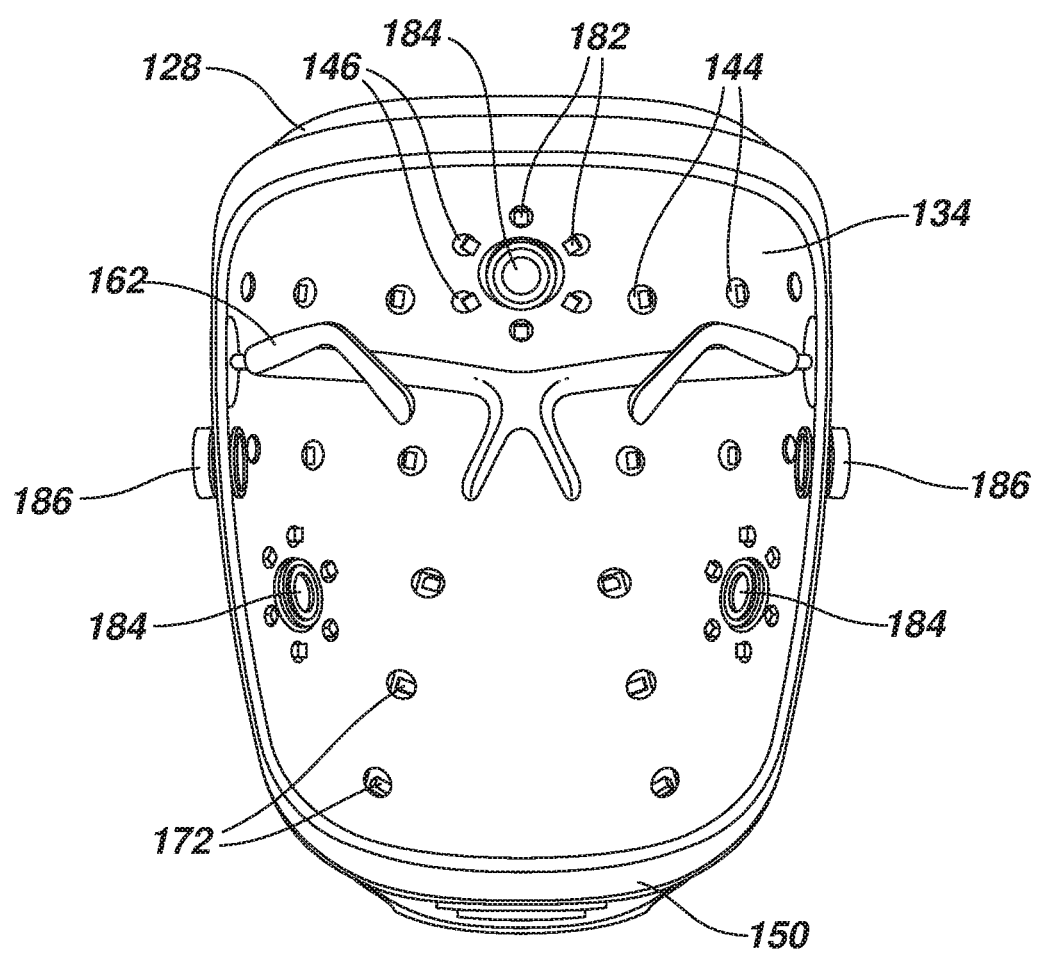
FIG. 13 is a rear view of the device of FIG. 10.

FIG. 9 is a front perspective view of a fully assembled first embodiment kit of the present invention. Data acquisition device 90 is coupled to adapter 92 which in turn is coupled to optical lens 84 of optical lens port 26 wearable lamp platform 10.

FIGS. 10-16 show a second embodiment of a wearable diagnostic treatment kit in the form of a wearable mask. In this embodiment, the kit includes a wearable lamp platform 100, a frame 160 for holding wearable lamp platform 100 in a fixed orientation spaced from the user's body, an adapter 192 arranged and configured to couple a data acquisition device to wearable lamp platform 100, and a power source controller 150 electrically coupled to the wearable lamp platform 100.

Wearable lamp platform 100 has an outer wall first surface 123 and an inner wall second surface 134, a plurality of treatment lamps 172 arranged and configured to irradiate a portion of a wearer's body, and first optical lens ports 126 and second optical lens ports 127, where ports 126 and 127 extend through lamp platform 100 from outer wall first surface 123 to inner wall second surface 134. Disposed in first optical lens ports 126 are first optical lenses 184. Disposed in second optical lens ports 127 are second optical lenses 188.

In this embodiment, wearable lamp platform 100 has a flexible skirt 128 disposed at one end of platform 100. Flexible skirt 128 is arranged and configured to block ambient light from the portion of a wearer's body under treatment. In other embodiments, flexible skirt 128 may be disposed about the periphery of wearable lamp platform 100 and arranged and configured to optically isolate the portion of a wearer's body from ambient light sources. In still other embodiments, wearable lamp platform 100 lacks a flexible skirt 128.

Inner wall second surface 134 of wearable lamp platform 100 is reflective and is arranged and configured to reflect light scattered by the wearer's body back to the body.

Figure 14:
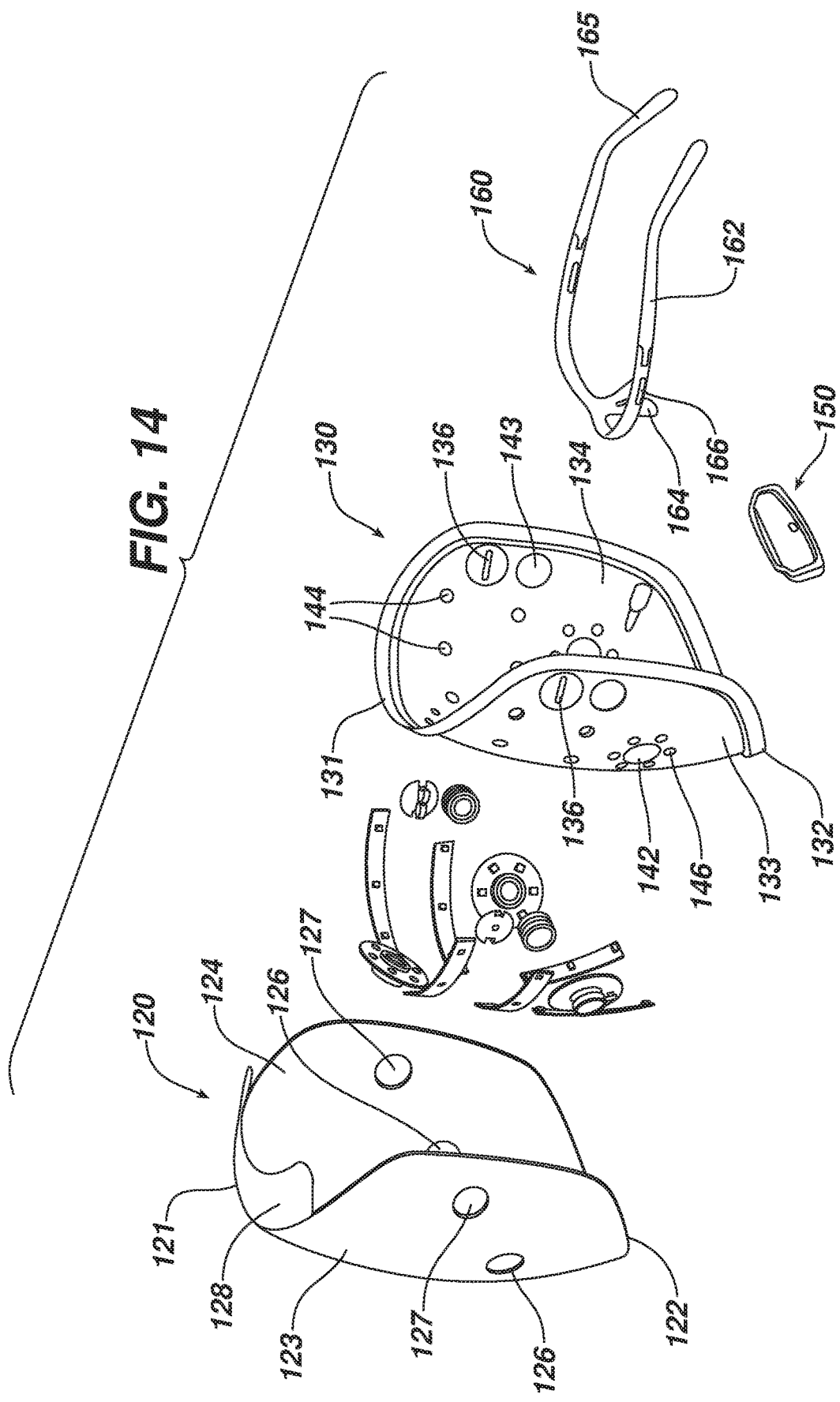
FIG. 14 is an exploded perspective view of FIG. 10.

FIG. 14 is an exploded perspective view of wearable lamp platform 100. As seen in the figure, wearable lamp platform 100 is comprised of an outer wall 120 and an inner wall 130. Outer wall 120 is disposed furthest away from the portion of the wearer's body receiving treatment, while the inner wall 130 is disposed closer thereto. The walls have a concave configuration in both horizontal and vertical directions, where the concavity comprises a multi-dimensional parabolic curvature for catching and reflecting the radiation back to the treatment areas. In this embodiment, where the treatment kit has the structure of a wearable mask, the walls are constructed of a plastic material having a malleable rigidity so that wearable lamp platform 100 can be bent and deflected slightly during use. It is intended that the concavity is slightly smaller than the head of the user so that the mask has to be bent out when applied thereby providing a close but comfortable tightness on the user which will keep the wearable lamp platform 100 in a desired position during use.

Outer wall 120 has a first end 121, a second end 122, an outer wall first surface 123, an outer wall second surface 124, first optical lens ports 126 and second optical lens ports 127 extending through outer wall 120, and flexible skirt 128 disposed on first end 121 of outer wall 120. As previously mentioned, flexible skirt 128 is arranged and configured to block ambient light from the portion of a wearer's body under treatment, and may be disposed about the periphery of wearable lamp platform 100 and arranged and configured to optically isolate the portion of a wearer's body from ambient light sources. Disposed in optical lens ports 126 are first optical lenses 184. Disposed in optical lens ports 127 are second optical lenses 188.

Inner wall 130 has a first end 131, a second end 132, an inner wall first surface 133, an inner wall second surface 134, snap-out pivotal connections 136, first optical lens ports 142, second optical lens ports 143, treatment lamp apertures 144, and image-acquisition lamp apertures 146. Ports 142 and 143, as well as apertures 144 and 146 all extend through inner wall 130. Inner wall 130 is comprised of a smooth seamless reflective surface facing the treatment area.

Outer wall 120 and inner wall 130 have different radii of concavity. When wearable lamp platform 100 is assembled, the entire perimeter is sealed as outer wall 120 and inner wall 130 come together. Such a mating seal is typically effected through a sonic weld arrangement. Alternatively, local sealing points (not shown) can be employed to assemble the walls together with spaced intermediate seals. As far as the user is concerned wearable lamp platform 100 presents an integral structure.

When wearable lamp platform 100 is assembled, treatment lamp apertures 144 are matingly aligned relative to treatment lamps 172 so that lamps 172 can radiate the therapeutic light through apertures 144. Accordingly, treatment lamps 172 are recessed relative to inner wall 130 to preclude contact with the treatment surface and to make it very difficult for treatment lamps 172 themselves to be in any way contacted by the user. Such an assembly results in a controlled communication of radiating therapy in a manner to impart a predetermined cone of therapeutic light on to a treatment area. The apertures are disposed relative to desired treatment areas and wall parabolic configuration for even light distributions across the treatment area. A combination of such a controlled cone of light, predetermined disposition of treatment lamps 172 themselves on lamp platform 100, an inner reflective surface on the inner wall 130, and a controlled positioning of the assembly relative to the treatment area via a platform position relative to contact areas of the nose and the ears, presents an assembly which presents a highly predictable distributive pattern of the light (predetermined cones of light per light source), thereby minimizing the number of treatment lamps 172 that need to be included for effective treatment.

Image-acquisition lamps 182 work in concert with first optical lenses 184 to acquire data pertaining to the user's body through first optical lenses 184. Image-acquisition lamps 182 also work in concert with second optical lenses 188 to acquire data pertaining to the user's body through second optical lenses 188. Since there is an offset between image-acquisition lamps 182 and second optical lenses 188, these lenses use images from angled lighting. Angled lighting generates a gradient of the illuminating field on the skin, enhancing the visualization of wrinkles and fine lines. By varying which sets of image-acquisition lamps 182 and second optical lenses 188 are used, different gradients are obtained. Using this method, different sets of wrinkles and fine lines may be visually enhanced.

Figure 15:
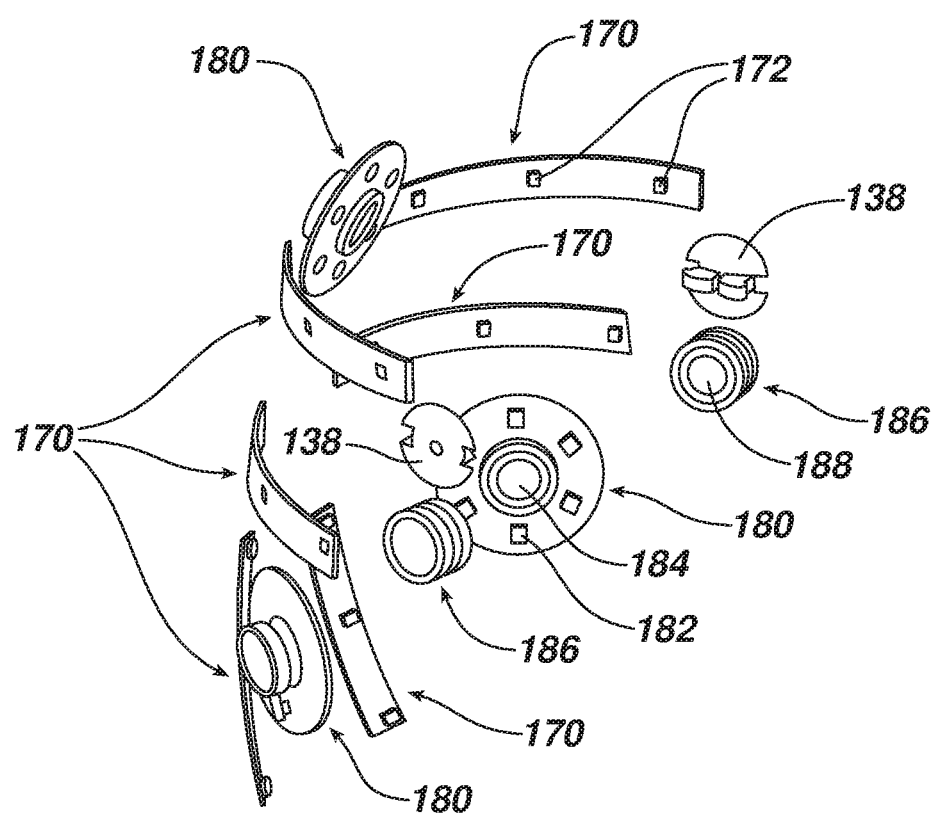
FIG. 15 is an exploded perspective view of a section of FIG. 14.

Also, when assembled, there is a spacing between outer wall 120 and inner wall 130 of wearable lamp platform 100. Disposed in the spacing, for enhanced safety and convenience purposes, are lamps, lenses and the circuitry connecting the lamps to power source controller 150. As shown in FIG. 15, treatment lamps 172 are disposed on treatment lamp platforms 170, image-acquisition lamps 182 and first optical lenses 184 are disposed on first image-acquisition platforms 180, and second optical lenses 188 are disposed on second image-acquisition platforms 186. Snap-out pivotal connection bodies 138 are also disposed in the spacing between outer wall 120 and inner wall 130. Though not shown in the drawings, circuitry connects power source controller 150 to treatment lamps 172 and image-acquisition lamps 182. The circuitry may be in the form of conductive wires or filaments.

In some embodiments, outer wall 120 primarily functions as a support for the lamps, lenses and the circuitry. Alternatively, the lamps could be fixed to the inner wall 130. Regardless of which wall supports the lamps, treatment lamps 172 need to be properly aligned with treatment lamp apertures 144, and image-acquisition lamps 182 must be disposed in image-acquisition lamp apertures 146 to achieve desired performance of wearable lamp platform 100.

When wearable lamp platform 100 is assembled, power source controller 150 is disposed on and attached to second end 122 of outer wall 120 and second end 132 of inner wall 130. Power source controller 150 has various components like resistors, ICs (Integrated Circuits), capacitors, transformers, switches, batteries, and other components. The source of power is typically batteries, which in some embodiments may be rechargeable.

Frame 160 is used for holding wearable lamp platform 100 in a fixed orientation spaced from the user's body. Frame 160 has temple arms 162, nose arms 164, and connectors 166. Temple arms 162 extend over the ears to keep frame 160 on the user's face. In this embodiment, formable ear latches 165 are included as part of the temple arms 162. Nose arms 164 hold wearable lamp platform 100 in a set distance from the user's face. Connectors 166 attach frame 160 to snap-out pivotal connections 136 on inner wall 130. In some embodiments, frame 160 may also have interchangeable lenses can be used to provide eye protection. In some embodiments, temple arms 162 may telescope for better sizing relative to the head size of the user, or could include a head strap to secure wearable lamp platform 100 to the user.

Snap-out pivotal connections 136 allow wearable lamp platform 100 to pivot relative to frame 160 so that a user may adjust light intensity relative to a treatment area by moving the platform closer or farther away. As noted above, platform 100 is flexible with a concave parabolic bias, but still has a malleable rigidity. When frame 160 is received on the user, it is disposed to expand platform 100 parabolic bias to form a match to the size of the user. Frame 160 reference contact points to the user may comprise the temples, the nose bridge and the ears of the user.

Treatment lamps 172 may be Light Emitting Diodes (LEDs), or other radiant energy forms, including fluorescents, lasers, infrareds, ultraviolet or combinations thereof. Methods of manipulating the light energy are encompassed within the present embodiments. Other methods of light emission may comprise continuous, pulsed, focused, diffuse, multi-wavelength, single wavelength, visible and/or non-visible light wavelengths.

Treatment lamps may provide blue light having a wavelength of between about 450 nm and about 495 nm, or red light having a wavelength of between about 620 nm and about 700 nm, or infrared light having a wavelength of between about 700 nm and about 1 mm. First embodiment wearable lamp platform 100 has a total of eighteen treatment lamps 172 arranged in an orderly pattern to cover the jaw line, chin, cheek, nose, and forehead, but not the eyelids of the user. The number, arrangement, type, and color of treatment lamps 172 depends on the desired treatment. Desired treatments include skin disorders such as acne vulgaris, atopic dermatitis, psoriasis, vitiligo, scleroderma, eczema, fine lines and wrinkles, as well as neonatal jaundice and some forms of cancer.

In some embodiments, the desired treatment is for skin acne. In this case, blue and red LEDs would be used, as these frequencies are most useful for acne treatment. A minimum number of treatment lamps 172 are intended, with there still being enough to provide effective treatment.

Image-acquisition lamps 182 work in concert with first optical lenses 184 and second optical lenses 188 to acquire data pertaining to the user's body. LEDs or other radiant energy forms may be used as image-acquisition lamps 182. In second embodiment wearable lamp platform 100, three sets of image-acquisition lamps 182 and first optical lenses 184 are shown, and two second optical lenses 188 are shown. In this embodiment, the first 184 and second 188 optical lenses are arranged to cover the chin, cheek, nose, and forehead. However, in other embodiments, the number of sets of image-acquisition lamps 182 and optical lenses 184, and the number of second optical lenses 188, as well as the arrangements of these sets, are possible, depending on the desired images. In addition, in some embodiments, one or more of first optical lens 184 or second optical lens 188 may be wide-angle lenses.

Second embodiment wearable lamp platform 100 has a total of eighteen image-acquisition lamps 182 arranged in a circular pattern around each first optical lens 184, and no image-acquisition lamps around any second optical lens 188. However, the number, arrangement, type, and color of image-acquisition lamps depends on the desired images.

Figure 16:
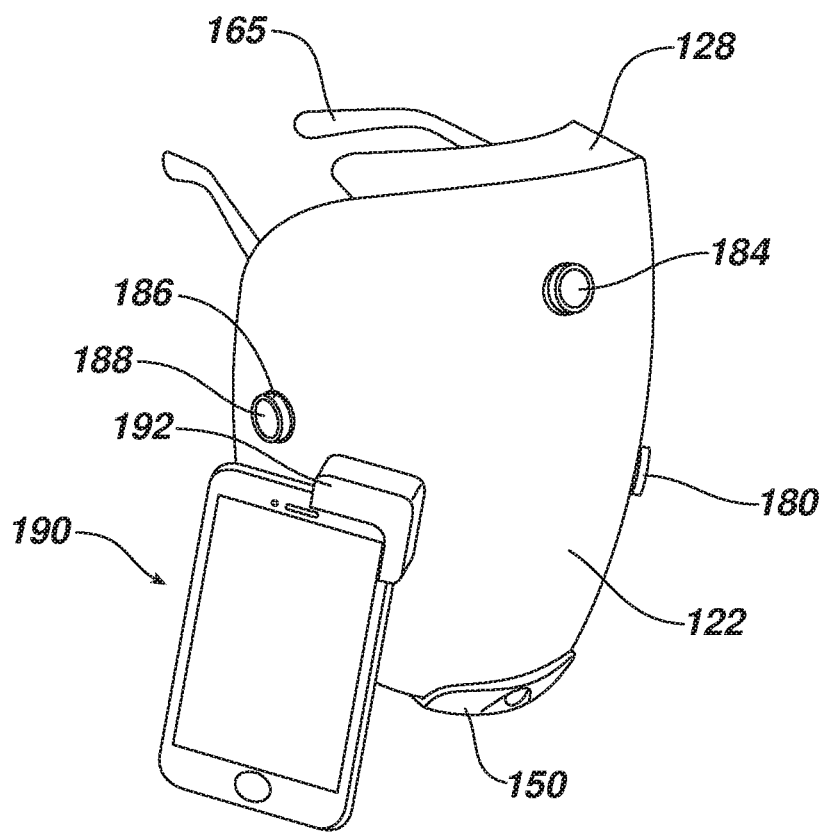
FIG. 16 is a front perspective view of the kit of FIG. 10 with the data acquisition device of FIG. 7 coupled to an optical lens of at least one port of the wearable lamp platform.

FIG. 16 is a front perspective view of one embodiment of a data acquisition device 190 that is coupled to wearable lamp platform 100 by adapter 192. Adapter 192 couples to any of the first optical lenses 184 disposed in any of first optical lens ports 126, or any of the second optical lenses 188 disposed in any of second optical lens ports 127. In some embodiments, data acquisition device 190 is a camera. In these embodiments, adapter 192 is selected to couple the camera lens of the camera to any of first optical lenses 184 disposed in any of first optical lens ports 126, or any of the second optical lenses 188 disposed in any of second optical lens ports 127. In other embodiments, such as that shown in FIG. 16, data acquisition device 190 is a smart phone. In these embodiments, adapter 192 is selected to couple the camera lens the smart phone to any of first optical lenses 184 disposed in any of first optical lens ports 126, or any of the second optical lenses 188 disposed in any of second optical lens ports 127.

In some embodiments, data acquisition device 190 has at least one data processing component. The data processing component can use visible light to analyzes skin color, polarized light to analyze surface or subsurface features of the skin, or ultraviolet light enhance the appearance of pigmentation, the bacteria p. acnes, and horns.

FIG. 16 is a front perspective view of a fully assembled second embodiment kit of the present invention. Data acquisition device 190 is coupled to adapter 192 which in turn is coupled to one of first optical lens 184 of first optical lens port 126 wearable lamp platform 100.

While the inner wall 30, 130 is described above having treatment lamp apertures 44, 144 aligned with treatment lamps 72, 172, one of ordinary skill will recognize that other light transmissive schemes may be used, such as light transmissive windows in the inner wall and even a continuously transmissive inner wall, such as a clear plastic inner wall.

Embodiments of first and second embodiment kits of the present invention will be used in the following manner to evaluate skin conditions, and deliver light-based skin therapy treatments for improving skin health.

In a first embodiment, the user first places adapter 92 on data acquisition device 90. The user then couples adapter 92 to at least one optical lens port 26 port of the wearable lamp platform 10, whereby image-acquisition lamps 82 are energized by the power source controller 50. Next, the user places the wearable lamp platform on a portion of a user's body, such as the face. Data acquisition device 90 is activated to acquire data pertaining to the user's body through optical lens 84. The data pertaining to the user's body is then analyzed to determine the course of present or future light treatment. If treatment is to be immediate, treatment lamps 72 are energized by the power source controller 50 and a treatment cycle is initiated.

As previously mentioned, treatment lamps 72 may be Light Emitting Diodes (LEDs), or other radiant energy forms, including fluorescents, lasers, infrareds, ultraviolet or combinations thereof. Methods of manipulating the light energy from treatment lamps 72 may include continuous, pulsed, focused, diffuse, multi-wavelength, single wavelength, visible and/or non-visible light wavelengths. The length of the treatment cycle will depend on treatment being performed. In some embodiments, treatment cycle is less than sixty (60) minutes, or thirty (30) minutes, or ten (10) minutes, or five (5) minutes, or one (1) minute. Once treatment is complete, the user removes the wearable lamp platform from a portion of a user's body, such as the face.

In some embodiments, prior to mask removal, image-acquisition lamps 82 are energized by the power source controller 50, and acquisition device 90 is activated to acquire data pertaining to the user's body through optical lens 84. This permits a "before and after" analysis. The user then removes the wearable lamp platform from a portion of a user's body, such as the face.

In some embodiments, the data acquired by acquisition device 90 is stored in the device, or in an external computer network such at the "cloud", for use in comparative analysis of treatment results over periods of hours, or days, or weeks, or months, or even years.

In a second embodiment, the user first places adapter 192 on data acquisition device 190. The user then couples adapter 192 to at least one first optical lens ports 126 or second optical lens ports 127 of wearable lamp platform 100, whereby some or all image-acquisition lamps 182 are energized by the power source controller 150. Next, the user places the wearable lamp platform on a portion of a user's body, such as the face. Data acquisition device 190 is activated to acquire data pertaining to the user's body through the appropriate first optical lenses 184 or second optical lenses 188. The data pertaining to the user's body is then analyzed to determine the course of present or future light treatment.

If treatment is to be immediate, treatment lamps 172 are energized by the power source controller 150 and a treatment cycle is initiated. The length of the treatment cycle will depend on treatment being performed. In some embodiments, treatment cycle is less than sixty (60) minutes, or thirty (30) minutes, or ten (10) minutes, or five (5) minutes, or one (1) minute. Once treatment is complete, the user removes the wearable lamp platform from a portion of a user's body, such as the face.

In some embodiments, prior to mask removal, image-acquisition lamps 182 are energized by the power source controller 150, and acquisition device 190 is activated to acquire data pertaining to the user's body through the appropriate first optical lenses 184 or second optical lenses 188. This permits a "before and after" analysis. The user then removes the wearable lamp platform from a portion of a user's body, such as the face.

In some embodiments, the data acquired by acquisition device 190 is stored in the device, or in an external computer network such at the "cloud", for use in comparative analysis of treatment results over periods of hours, or days, or weeks, or months, or even years. This allows the user or a health care professional to compare skin conditions over time. In embodiments in which the data is stored in an external computer network, the acquisition device 190 is in communication, either wired or wireless, to the such network.

Example

A Neutrogena® Light Therapy Acne mask (Johnson & Johnson Consumer Inc., Skillman, N.J.) was retrofitted for this application. Three half-inch diameter holes were stamped through the inner and outer walls of the mask, avoiding the treatment LEDs positioned near the cheeks and forehead.

Three circular rigid PCB boards were fabricated with a 0.5-inch diameter through hole by Technology By Design (Doylestown, Pa.) using the Cadence OrCAD PCB design software. Three white and three near-UV LEDs 82 were attached to the rigid PCB board equally spaced around the central through hole. A 160° Fisheye Lens 84 (PL-A2, Aukey, Shenzhen, Guangdong, China) was mounted in each rigid PCB board through hole. A Wratten #15 yellow filter (Kodak, Rochester, N.Y.) was fixed to the inner surface of each lens. Each board had 2 magnets fixed to the side opposite the LEDs to aid in alignment of the adapter 92 and a hall sensor to initiate illumination as the adapter was brought in contact with the imaging lens 84.

The circular rigid PCB boards with image-acquisition LEDs, lens, and filter 80 were mounted between the outer wall first surface and inner wall second surface so that the LEDs lined up with image-acquisition lamp apertures 46. A rigid board for the BLUETOOTH module and the charging module was fixed to the bottom of the platform with parabolic bias. A Li-ION battery was also mounted to the rigid board.

An adapter 92 designed to fit around the rear-facing camera on an iPhone® 6 (Apple Inc., Cupertino, Calif.) smartphone was cast using stereolithography. Three magnets were mounted on the adapter. Two of the magnets helped to align the adapter in a fixed position, relative to the imaging lens 84. When correctly aligned, the third magnet lined up with the hall sensor to turn on the image-acquisition LEDs for that lens.

The retrofitted mask was worn by a test subject. An Apple® iPhone® 6 smartphone was then disposed on the image-acquisition platform 80 located on the right cheek of the mask as shown in FIG. 9. The image-acquisition system was activated, and images of the user's right cheek were stored in the memory of the iPhone® 6 smartphone.

What is claimed is:

1. A method of evaluating skin comprising the steps of:
   (a) coupling an adapter to a port of a wearable lamp platform having an outer surface and an inner surface, the port having disposed therein an optical lens and having a plurality of image image-acquisition lamps disposed around the optical lens, whereby the image-acquisition lamps are energized by a power source electrically coupled to the wearable lamp platform, and the wearable lamp platform comprises a plurality of treatment lamps arranged and configured to irradiate a portion of a wearer's body;
(b) placing the wearable lamp platform on a portion of a user's body;
(c) coupling a data acquisition device to the adapter and activating the data acquisition device to acquire data pertaining to the user's body through the optical lens;
(d) analyzing the data pertaining to the user's body;
(e) determining a light treatment regimen for the user's body; and
(f) applying light treatment to the user's body according to the determined light treatment regimen.

2. The method of claim 1 wherein the inner surface of the wearable lamp platform is reflective and is arranged and configured to reflect light scattered by the wearer's body back to the body.

3. The method of claim 1 wherein the plurality of treatment lamps of the wearable lamp platform comprises treatment lamps that provide blue light having a wavelength of between about 450 nm and about 495 nm.

4. The method of claim 1 wherein the plurality of treatment lamps of the wearable lamp platform comprises treatment lamps that provide red light having a wavelength of between about 620 nm and about 700 nm.

5. The method of claim 1 wherein the plurality of treatment lamps of the wearable lamp platform comprises treatment lamps that provide infrared light having a wavelength of between about 700 nm and about 1 mm.

6. The method of claim 1 wherein the step of coupling a data acquisition device to the adapter comprises coupling a camera to the adapter.

7. The method of claim 6 wherein the camera comprises at least one data processing component.

8. The method of claim 6 wherein step of coupling a data acquisition device to the adapter comprises coupling a smart phone to the adapter.

9. The method of claim 1 wherein the step of analyzing the data pertaining to the user's body comprises analyzing data pertaining to wrinkles.

10. The method of claim 1 wherein the step of analyzing the data pertaining to the user's body comprises analyzing data pertaining to acne.

11. The method of claim 1 wherein the step of analyzing the data pertaining to the user's body comprises analyzing data pertaining to skin tone.

12. The method of claim 1 further comprising the step of communicating data to an external network.

13. The method of claim 12 further comprising comparing skin conditions over time.

14. The method of claim 1 further comprising the step of controlling the plurality of treatment lamps to provide at least two distinct wavelength bands to irradiate the portion of the wearer's body.

15. The method of claim 1 further comprising the step of coupling the adapter and data acquisition device to a second port of the wearable lamp platform.

\* \* \* \* \*